United States Patent [19]

Healy

[11] 4,331,153
[45] May 25, 1982

[54] DISPOSABLE EKG ELECTRODE

[76] Inventor: James W. Healy, 6462 Surfside Way, Malibu, Calif. 90265

[21] Appl. No.: 206,528

[22] Filed: Nov. 13, 1980

[51] Int. Cl.³ .............................................. A61B 5/04
[52] U.S. Cl. .................................................... 128/641
[58] Field of Search ............................. 128/639–641, 128/644, 798, 802, 803

[56] References Cited

U.S. PATENT DOCUMENTS

| | | | |
|---|---|---|---|
| 4,029,086 | 6/1977 | Corasanti | 128/641 |
| 4,265,253 | 5/1981 | Abraham | 128/803 X |
| 4,270,544 | 6/1981 | Gilden et al. | 128/640 |

Primary Examiner—Lee S. Cohen
Attorney, Agent, or Firm—Ralph B. Pastoriza

[57] ABSTRACT

A disposable EKG electrode pad is provided with a cut to enable an auxiliary portion of the pad to be lifted out of the plane of the main pad portion. By this arrangement, the main pad portion is pressed against the patient's skin and the auxiliary pad portion lifted up and placed over the snap fastener cable extending from the electrode projection on the main portion to hold this cable securely to the patient's skin adjacent to the main portion of the pad. Relative movement between the snap fastener and electrode projection on the pad is thus inhibited and thereby artifacts are avoided.

2 Claims, 5 Drawing Figures

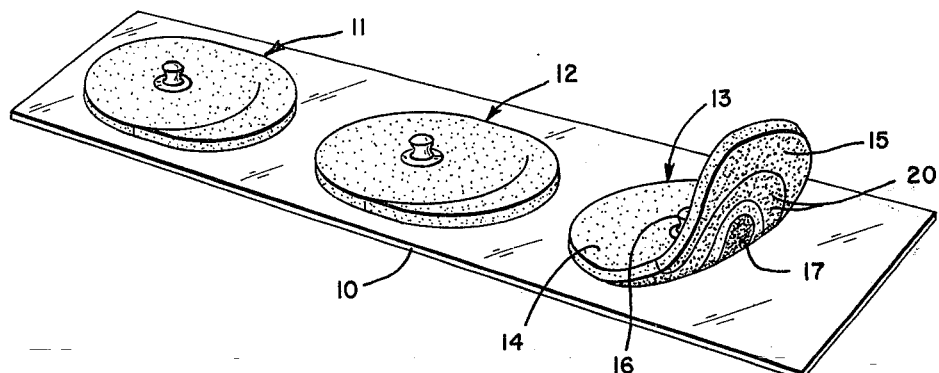
FIG. 1
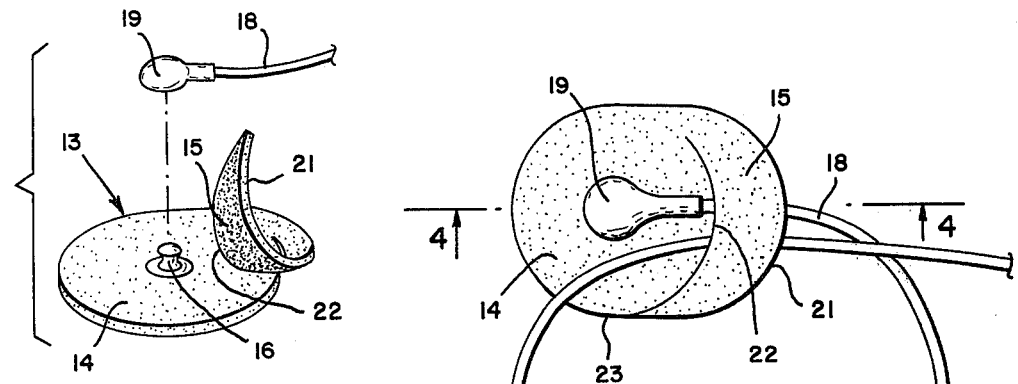
FIG. 2
FIG. 3
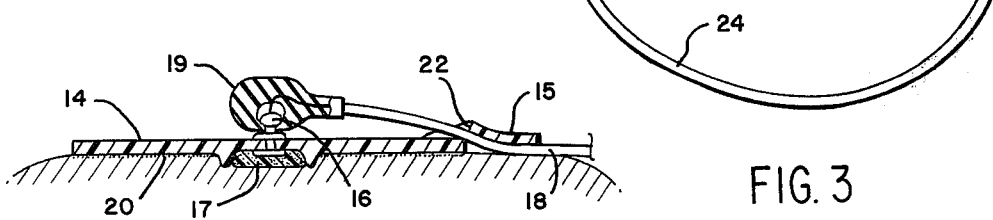
FIG. 4
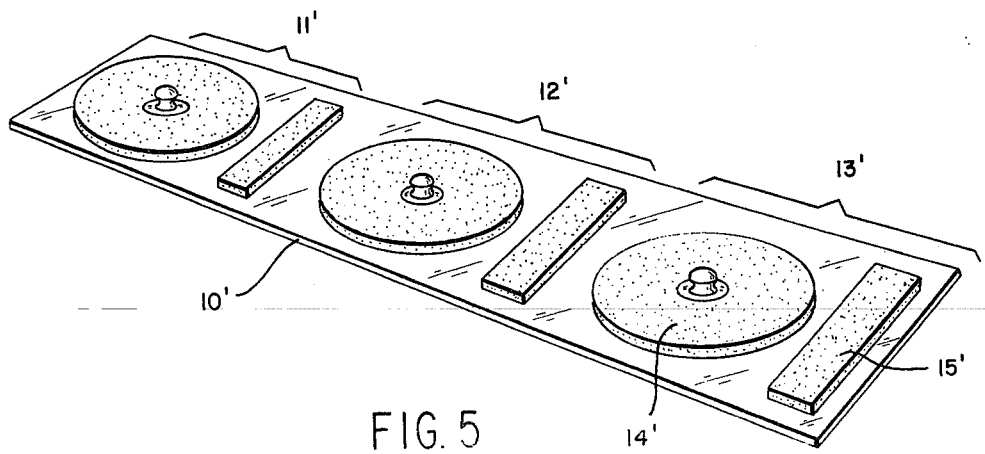
FIG. 5

DISPOSABLE EKG ELECTRODE

This invention relates generally to medical devices and more particularly to an improved disposable-type EKG electrode.

BACKGROUND OF THE INVENTION

Most present day EKG electrodes are of the disposable type and comprise a pad member with an electrode projection on its top surface and adhesive material on its bottom surface except for a central portion containing a conductive jelly for making good electrical contact with a patient's skin when the pad is pressed in place. A cable terminating in an electrode snap fastener is connected to the electrode projection on the pad so that proper electrical connection is effected. Several such disposable electrode pads are located at strategic positions on the patient's torso and small electrical signals indicative of the patient's heartbeat can be properly recorded to form an electrocardiogram for the patient.

After the electrocardiogram has been completed, the cable electrode snap fasteners are removed from the electrode projections on the electrode pad and these pads simply removed from the patient's torso and thrown away.

Problems currently experienced with present day EKG electrodes may be summarized as follows:

1. Artifacts (spurious signals) are caused by relative movement between the electrode projection and the electrode snap fastener resulting from movement of the lead wire or cable extending from the snap fastener. Such movement can be a result of the relatively long cables used in some instances as well as from the movements of the patient.
2. Artifacts are also generated when the impedance between the metallic electrode projection and the patient's skin changes. Such impedance change is caused by an increased space between the skin and electrode projection when the lead wire or cable is pulling against the electrode.
3. Patient movements often cause the breakage of lead wires due to tension.
4. Because of the freedom of movement of the cable, there is wear on the cable and frequent replacement is often necessary.

The foregoing problems have plagued the hospital industry since the inception of disposable type electrodes. Attempts to solve these problems have taken the form of utilizing large quantities of adhesive tape to tape the lead wires or cables to the patient's torso. For example if portions of the cable extending from the snap electrode could be taped to the patient's torso it is clear that relative movements between the snap fastener and the electrode projection itself would be substantially reduced since movements of the remaining portions of the cable beyond those portions fastened to the patient's torso would have little effect on the connecting portions to the electrodes. However, utilizing conventional adhesive tape in this manner has brought along many new problems. For example, the large quantity of adhesive tape for each of the electrodes involved (and there may be 4-6 electrodes during any one recording session) obstructs other diagnostic procedures including defibrillation. Further, the adhesive tape itself is irritating to the patient and requires shaving of a large skin area if it is to be effective in adhering to the skin. This latter problem creates another problem in the increased cost and time for skin preparation. Finally, there is general discomfort to the patient when the various cables or lead wires are mass-taped to his skin.

BRIEF DESCRIPTION OF THE PRESENT INVENTION

With the foregoing in mind, the present invention contemplates an improved disposable type EKG electrode which avoids the foregoing problems by simply utilizing a part of the electrode itself to securely hold the lead wire or cable. Essentially by a simple one-step procedure, the electrode of this invention eliminates relative motion between the electrode projection and snap fastener, prevents "lifting" of the electrode snap fastener and insures that tension against the snap does not change the electrode impedance.

Briefly, the electrode includes a pad having an electrode projection on its top surface and an adhesive backing on its bottom surface for securement to the skin of the patient. A portion of this pad can be isolated from the remaining portion of the pad by means of a cut formed in the pad. This portion is shaped to enable adhesive holding against the patient's skin of a portion of the electrode cable extending from the snap fastener when the snap fastener is received on the electrode projection. Relative movements between the snap fastener and the electrode projection are thus substantially eliminated and thus the generation of artifacts is similarly eliminated.

BRIEF DESCRIPTION OF THE DRAWINGS

A better understanding of this invention as well as further features and advantages thereof will be had by referring to the accompanying drawings in which:

FIG. 1 is a perspective view of a plastic carrier sheet for packaging and/or shipping a plurality of disposable type EKG electrodes designed in accord with the present invention, one of the electrodes being shown in partially removed position from the carrier sheet;

FIG. 2 is an exploded perspective view of one of the electrodes of FIG. 1 preparatory to being used on a patient;

FIG. 3 is a top plan view of the electrode of FIG. 2 after the same has been secured to a patient in the taking of an electrocardiogram;

FIG. 4 is a cross section taken in the direction of the arrows 4—4 of FIG. 3; and, FIG. 5 is a perspective view of a plastic carrier sheet for holding modified disposable EKG electrodes designed in accord with this invention.

DETAILED DESCRIPTION OF THE INVENTION

A preferred embodiment of this invention is illustrated in FIG. 1 wherein there is shown a plastic carrier sheet 10 for supporting a plurality of disposable EKG electrodes designated generally by the numerals 11, 12 and 13. The arrangement is such that the electrodes are readily manually accessible and can be successively peeled off from the plastic carrier strip 10 when they are to be used.

Each of the electrodes illustrated in FIG. 1 is identical and therefore a detailed description of one will suffice for all.

Considering by way of example the specific electrode 13 as illustrated in FIG. 1 as well as in FIGS. 2, 3 and 4, the same comprises a pad of pliable material including a main portion 14 and an auxiliary portion 15. An electrode projection 16 is carried on the top surface of the main portion 15 while a conductive jelly 17 is carried on the bottom surface of the main portion, this conductive jelly being in electrically conductive relationship through the main portion 14 of the pad with the electrode projection 16.

As shown best in FIG. 2, the electrode 13 cooperates with an electrical cable 18 extending from an appropriate recording device (not shown) terminating in an electrode snap fastener 19 arranged to be received over the electrode projection 16 to thereby connect the cable 18 to the conductive jelly and thus to the patient's skin when the pad 13 is pressed to the patient's skin.

In order to secure the pad to a specific area of the patient's skin, the area in question is normally shaved clean of hair and the pad then firmly pressed into place on the shaved area. An appropriate adhesive material shown at 20 in FIG. 1 covers the remaining portion of the bottom surface of the pad not covered by the conductive jelly 17.

Referring to both FIGS. 2 and 3 together, in the preferred embodiment shown the auxiliary portion 15 is defined between one edge 21 of the pad and a cut 22 formed in the pad extending from an adjacent edge 23 towards an opposite edge and terminating short of the opposite edge as most clearly shown in FIG. 3. The arrangement is such that the auxiliary portion 15 can then be lifted out of the plane of the main portion 14 of the pad as shown in FIG. 2.

With the foregoing arrangement, the bottom surface of the main portion 14 of the pad can be pressed against a patient's skin as described so that the conductive jelly will bear against the skin in conductive relationship. The auxiliary portion 15 of the pad is then lifted up as shown in FIG. 2 and utilized to overlie at least one portion of the cable 18. The auxiliary portion 15 can then be pressed down against the patient's skin and it will be evident that the one portion of the cable held is adjacent to the electrode snap fastener and thus will serve to hold the snap fastener essentially immobile relative to the electrode projection.

The foregoing arrangement is clearly shown in FIG. 3 wherein an additional loop 24 of the cable 18 is also shown held by the auxiliary portion 15. It is not necessary that there be provided an additional loop 24 to prevent immobility between the electrode snap fastener 19 and the electrode projection 16 but the extra loop is illustrated in FIG. 3 merely to indicate that should the cable be longer than necessary, the same can be looped to take up slack and thus lessen the risk of movement of the cable during recording.

Referring to FIG. 4, there is shown the snap fastener 19 over the electrode projection 16 and it can be appreciated that if the cable 18 were not taped down by the auxiliary portion 15 as shown in FIG. 4, rotation, tilting and upward and downward translation movements of the snap fastener 19 relative to the electrode projection 16 could all result in spurious signals not only from changes in contact pressure and thus conductivity but changes in impedance between the conductive jelly and the skin area particularly when the electrode is subject to tension by the snap fastener tending to pull it away from the skin.

By providing the auxiliary portion in the manner described, by means of a simple arcuate cut formed into a side of the pad, the auxiliary portion is conveniently available for immediate use in taping down the one cable portion extending from the snap fastener. However, it should be understood it would be possible to have the auxiliary portion physically separated from the main pad portion and simply in the form of an elongated strip which could be used to hold the cable in the manner described in FIG. 3.

Such an arrangement as the foregoing, is shown in the modified version illustrated in FIG. 5 wherein there is shown a plastic carrier sheet 10' for holding electrode pads 11', 12' and 13' each comprised of main portions and auxiliary portions such as indicated at 14' and 15' for the electrode 13'. The material of the portion 15' is identical to the portion 14'. Being provided with an adhesive underside and being positioned next to the main portion 14', it is readily available when the electrode 14' is attached to a person's skin, both portions being peeled away from the plastic carrier sheet simultaneously or one immediately after the other.

From all of the foregoing, it will now be evident that the present invention has provided in a very simple manner a modified disposable EKG electrode which exhibits a surprising and remarkable number of advantages in that various problems heretofore involved with conventional electrodes are overcome. The solution proposed by my present invention is not only extremely simple but inexpensive and does not require any appreciable changes in manufacturing technique.

The preferred embodiment, as described, involves having the auxiliary portion used for holding the cable as an integral part of the main portion but so shaped as by means of the cut as to be readily usable. However, the principal advantages of the present invention can be realized by providing a separate elongated strip on a plastic carrier sheet so that it is always next to and available to the main electrode portion to be secured to the patient, all as described in conjunction with FIG. 5.

While circular and oval shapes have been shown as well as rectangular and arcuate shapes for the auxiliary portions, the invention is not limited to these specific outlines which are set forth merely as examples of the disposable electrode.

I claim:

1. A disposable EKG electrode, including, in combination:
   (a) a pad of pliable material including a main portion and an auxiliary portion defined between one edge of the pad and a cut formed in the pad extending from an adjacent edge towards an opposite edge and terminating short of the opposite edge so that part of the auxiliary portion can be lifted away from the plane of the main portion;
   (b) an electrode projection carried on the top surface of the main portion;
   (c) a conductive jelly carried on the bottom surface of said main portion in electrically conductive contact through the main portion with said electrode projection so that a cable terminating in an electrode snap fastener received on said projection is electrically connected to said conductive jelly; and,
   (d) an adhesive material on the remaining portion of the bottom surface of the pad not covered by said conductive jelly whereby the bottom surface of the main portion of the pad can be pressed against a patient's skin so that the conductive jelly is held against the skin by the adhesion of the main portion of the pad to the skin and the auxiliary portion of the pad lifted away from the plane of the main portion so that the cable can be passed under the auxiliary portion so that the auxiliary portion will overlie at least one portion of the cable extending from the snap fastener and hold the same to the patient's skin so as to inhibit relative movements between the snap fastener and electrode projection when portions of the cable beyond said one portion move and thereby avoid generation of artifacts.

2. The subject matter of claim 1, in which there is provided in combination a plastic carrier sheet against which the bottom surface of the pad is pressed to carry the pad during shipment, additional pads being supported and carried by said same sheet so that as the electrodes are to be used, they can successively be peeled away from the plastic carrier sheet.

* * * * *